(12) United States Patent
Liu et al.

(10) Patent No.: US 10,973,454 B2
(45) Date of Patent: Apr. 13, 2021

(54) METHODS, SYSTEMS, AND APPARATUS FOR IDENTIFYING AND TRACKING INVOLUNTARY MOVEMENT DISEASES

(71) Applicant: International Business Machines Corporation, Armonk, NY (US)

(72) Inventors: Su Liu, Austin, TX (US); Kai Liu, Malden, MA (US); Romelia H. Flores, Keller, TX (US); Cheng Xu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 339 days.

(21) Appl. No.: 16/058,807

(22) Filed: Aug. 8, 2018

(65) Prior Publication Data

US 2020/0046280 A1    Feb. 13, 2020

(51) Int. Cl.
*A61B 5/00*         (2006.01)
*A61B 5/11*         (2006.01)
*G16H 50/20*     (2018.01)

(52) U.S. Cl.
CPC .......... *A61B 5/4082* (2013.01); *A61B 5/0077* (2013.01); *A61B 5/1101* (2013.01); *A61B 5/1128* (2013.01); *A61B 5/4842* (2013.01); *A61B 5/7275* (2013.01); *A61B 2562/0219* (2013.01); *A61B 2562/0247* (2013.01); *G16H 50/20* (2018.01)

(58) Field of Classification Search
CPC ........ G16H 50/20; G16H 50/00; G16H 50/30; G16H 80/00; G16H 40/67; G16H 20/30; A61B 2562/0247; A61B 2562/0219; A61B 5/7289; A61B 5/7285; A61B 5/7282; A61B 5/7278; A61B 5/7275; A61B 5/7271; A61B 5/4842; A61B 5/1128; A61B 5/1127; A61B 5/1126; A61B 5/1125; A61B 5/1124; A61B 5/1101; A61B 5/11; A61B 5/0077; A61B 5/4088; A61B 5/4082; A61B 5/4076
See application file for complete search history.

(56) References Cited

U.S. PATENT DOCUMENTS

| | | | |
|---|---|---|---|
| 7,479,949 | B2 | 1/2009 | Jobs et al. |
| 8,059,101 | B2 | 11/2011 | Westerman et al. |
| 8,174,503 | B2 | 5/2012 | Chin |
| 8,902,181 | B2 | 12/2014 | Hinckley et al. |
| 9,427,175 | B2 | 8/2016 | Halkias et al. |
| 9,687,189 | B2 | 6/2017 | Tafazzoli et al. |

(Continued)

OTHER PUBLICATIONS

G. Chang, "8 Smart Parkinson's apps you need to try", Parkinson's Life, Apr. 14, 2015, pp. 1-9.

(Continued)

*Primary Examiner* — Matthew Kremer
*Assistant Examiner* — Avery M Foley
(74) *Attorney, Agent, or Firm* — Kunzler Bean & Adamson

(57) ABSTRACT

Methods that can that can identify involuntary movement diseases are provided. One method includes sensing, by a set of sensors of a computing device, behavior of a user while the user interacts with the computing device and identifying, by a processor of the computing device, involuntary movement patterns for the user based on one or more characteristics of the sensed behavior. Systems and apparatus that can include, perform, and/or implement the methods are also provided.

19 Claims, 9 Drawing Sheets

(56) References Cited

U.S. PATENT DOCUMENTS

| | | | |
|---|---|---|---|
| 9,872,637 | B2 | 1/2018 | Kording et al. |
| 9,974,478 | B1* | 5/2018 | Brokaw ................. A61B 5/486 |
| 2015/0196232 | A1 | 7/2015 | Mitsi et al. |
| 2016/0000323 | A1 | 1/2016 | Myr |
| 2016/0106344 | A1 | 4/2016 | Nazari |
| 2016/0135751 | A1 | 5/2016 | Valacich et al. |
| 2016/0331295 | A1 | 11/2016 | Kozloski et al. |
| 2019/0110754 | A1* | 4/2019 | Rao .......................... G06N 3/08 |

OTHER PUBLICATIONS

W. Adams, "High-accuracy detection of early Parkinson's Disease using multiple characteristics of finger movement while typing", PLOS one, http://journals.plos.org/plosone/article?id=10.1371/journal.pone.0 . . . , Nov. 30, 2017, pp. 1-13.

Stanford Medicine, "Involuntary Movements", Stanford Medicine 25, https://stanfordmedicine25.stanford.edu/the25/im.html, known about as early as and downloaded on May 2, 2018, pp. 1-9.

* cited by examiner

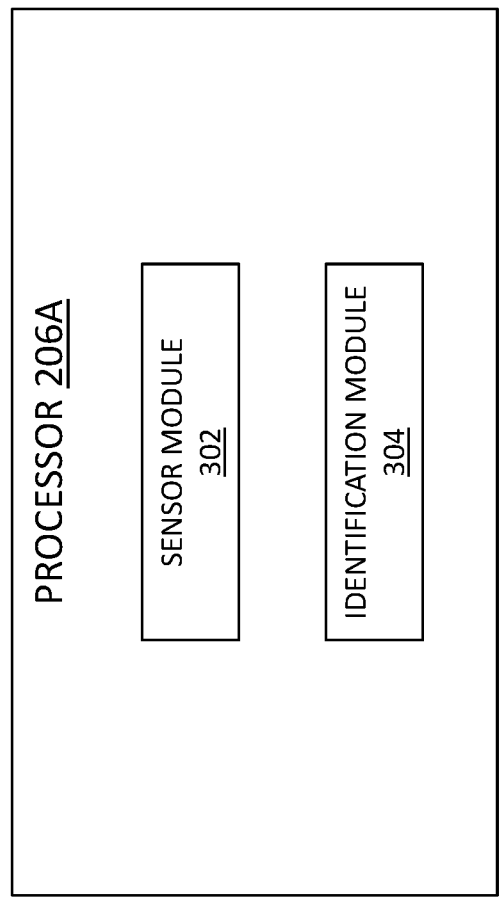

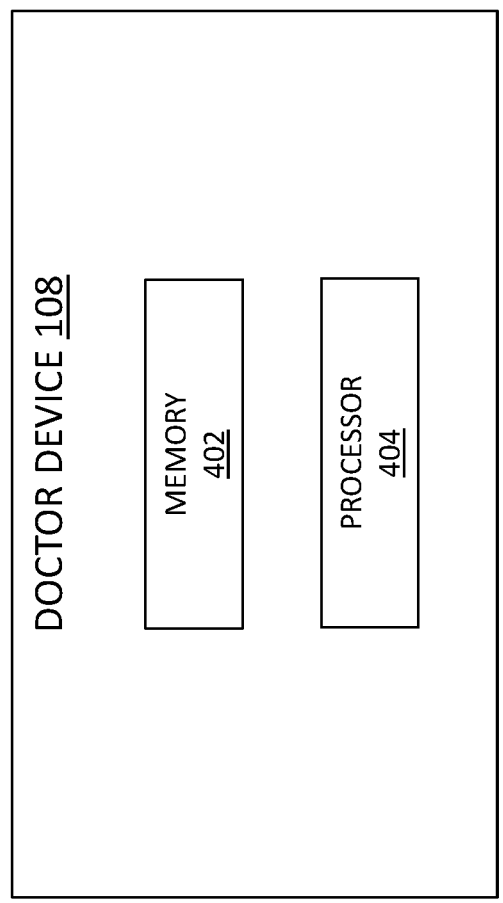

METHODS, SYSTEMS, AND APPARATUS FOR IDENTIFYING AND TRACKING INVOLUNTARY MOVEMENT DISEASES

FIELD

The subject matter disclosed herein relates to computing systems and devices and, more particularly, relates to methods, systems, and apparatus that can identify and track involuntary movement diseases.

BACKGROUND

There are numerous types of involuntary movement diseases that are associated with various health problems. There are several potential causes of the involuntary movements that are characteristic of the various involuntary movement diseases. In general, involuntary movement suggests that there may be damage to nerves and/or areas of the brain that affect motor coordination. Individuals experiencing involuntary movements can require constant or regular attention/supervision so they do not injure themselves.

To identify whether an individual is experiencing one or more involuntary movements, medical professionals usually conduct a set of diagnostic tests to determine if the individual's movements are characteristic of a particular involuntary movement disease.

Often, involuntary movements and, hence, involuntary movement diseases can be difficult to identify and/or diagnose. In fact, no specific tests exist to definitively identify and/or diagnose some involuntary diseases (e.g., Parkinson's disease). In addition, some diagnosis testing can consume large amounts of time, involve a long testing process, involve regular appointments, and may include a large quantity and high frequency of follow-up appointments to evaluate and track the condition and/or symptoms over time.

Another factor that can add to the difficulty in identifying and/or diagnosing involuntary movement diseases is the fact that some involuntary movement disease symptoms are similar to other illnesses. For example, symptoms of Tardive Dyskinesia (TD) can be similar to schizophrenia, Attention Deficit Hyperactivity Disorder (ADHD), and Tourette syndrome.

Once diagnosed with an involuntary movement disease, an individual often requires precise and timely follow-up appointments with medical professionals to ensure effective treatment. Further, disease deterioration generally can and frequently does occur during treatment. These factors can complicate the treatment process and/or make it difficult to comprehensibly monitor an individual's reaction and/or progress during treatment.

Currently, there are applications that can assist in diagnosing involuntary movement diseases (e.g., Parkinson mPower, Parkinson's Central, and Lift Pulse). However, these applications and their associated devices and systems are limited in their ability to identify, track, diagnose, and facilitate treatment of the various involuntary movement diseases and their respective characteristics.

BRIEF SUMMARY

Methods, systems, and apparatus that can identify and track involuntary movement diseases are provided. One method includes sensing, by a set of sensors of a computing device, behavior of a user while the user interacts with the computing device and identifying, by a processor of the computing device, involuntary movement patterns for the user based on one or more characteristics of the sensed behavior.

A system includes a first computing device including a processor in which the processor is configured to sense behavior of the user while the user operates the first computing device and identify involuntary movement patterns for the user based on the sensed behavior. The system further includes a storage device coupled to the first computing device in which the storage device is configured to store identified involuntary movement patterns for the user and a second computing device coupled to the storage device in which the second computing device is configured to access the identified involuntary movement patterns stored in the storage device and transmit health data generated by a health professional to the user. In various embodiments, the storage device is located remotely from the first computing device and the health data is based on the identified involuntary movement patterns and includes data related to one of a plurality of involuntary movement diseases.

One apparatus includes a set of sensors that sense behavior of a user while the user interacts with the apparatus and an identification module that identifies involuntary movement patterns for the user based on one or more characteristics of the sensed behavior. In various embodiments, at least a portion of the identification module includes one or more of a set of hardware circuits, a set of programmable hardware devices, and executable code stored on a set of non-transitory computer-readable storage mediums.

BRIEF DESCRIPTION OF THE DRAWINGS

So that at least some advantages of the technology may be readily understood, more particular descriptions of the embodiments briefly described above are rendered by reference to specific embodiments that are illustrated in the appended drawings. Understanding that the drawings included herein only depict some embodiments, the embodiments discussed herein are therefore not to be considered as limiting the scope of the technology. That is, the embodiments of the technology that are described and explained herein are done with specificity and detail utilizing the accompanying drawings, in which:

FIGS. 3A and 3B are block diagrams of various embodiments of a processor included in the patient device of FIG. 2:

FIG. 4 is a block diagram of one embodiment of a doctor device included in the healthcare network of FIG. 1:

DETAILED DESCRIPTION

Figure 1:
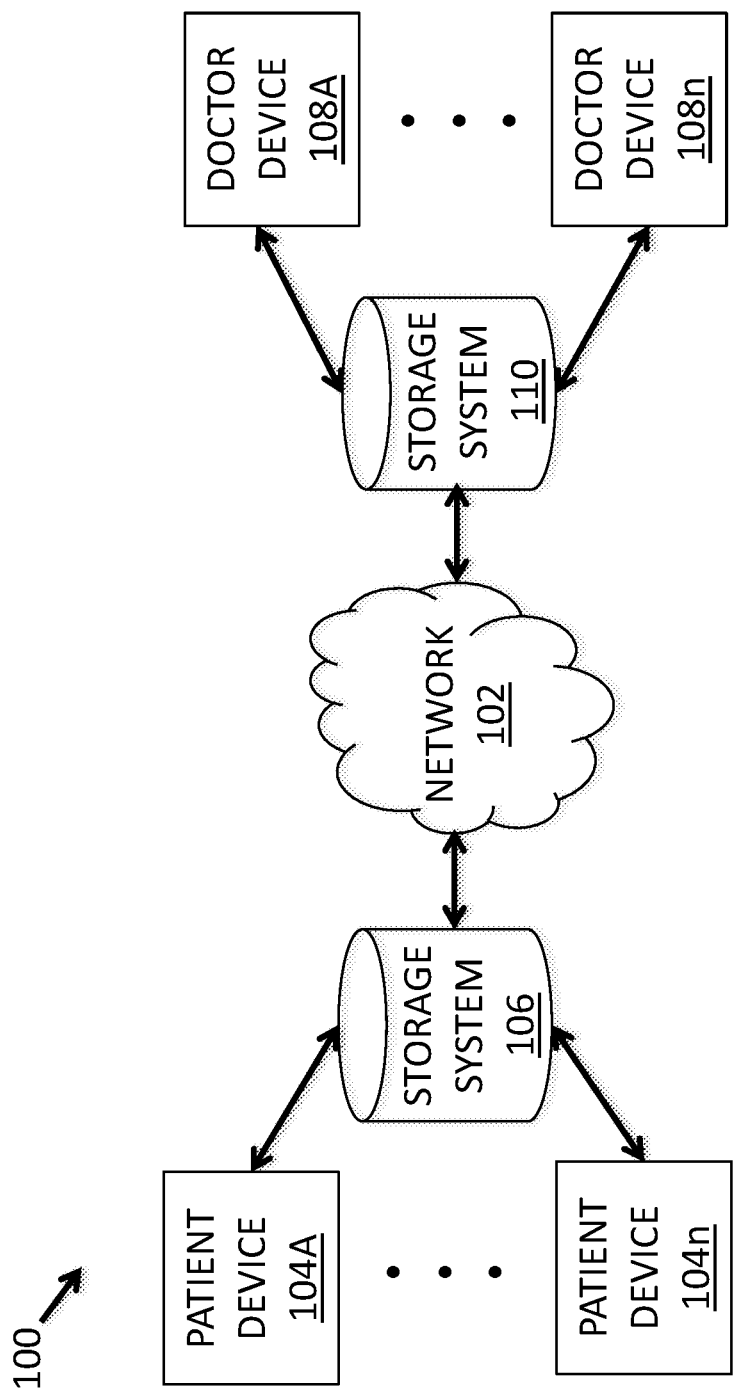
FIG. 1 is a block diagram of one embodiment of a healthcare network.

Disclosed herein are various embodiments providing methods, systems, and computer program products that can merge protocols for storage networks and systems. Notably, the language used in the present disclosure has been principally selected for readability and instructional purposes, and not to limit the scope of the subject matter disclosed herein in any manner.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "including," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more," unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Further, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present technology may be a system, a method, and/or a computer program product. The computer program product may include a computer-readable storage medium (or media) including computer-readable program instructions thereon for causing a processor to carry out aspects of the present technology.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove including instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fibre-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibres, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). To perform aspects of the present technology, in some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry.

Aspects of the present technology are described herein with reference to flowchart illustrations and/or block diagrams of methods, apparatus (systems), and computer program products according to embodiments of the technology. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium including instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technology. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

To more particularly emphasize their implementation independence, many of the functional units described in this specification have been labeled as modules. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

The schematic flowchart diagrams and/or schematic block diagrams in the Figures illustrate the architecture, functionality, and operation of possible implementations. It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Although various arrow types and line types may be employed in the flowchart and/or block diagrams, they are understood not to limit the scope of the corresponding embodiments. Indeed, some arrows or other connectors may be used to indicate only an exemplary logical flow of the depicted embodiment.

The description of elements in each figure below may refer to elements of proceeding figures. For instance, like numbers can refer to similar elements in all figures, including alternate embodiments of similar elements.

With reference now to the drawings, FIG. 1 is a block diagram of one embodiment of a healthcare network 100 (or system) including a network 102 connecting a set of patient devices 104A through 104*n* and a storage system 106 to a set of doctor devices 108A through 108*n* and a storage system 110. The network 102 may be any suitable wired and/or wireless network 102 (e.g., public and/or private computer networks in any number and/or configuration (e.g., the Internet, an intranet, a cloud network, etc.)) that is known or developed in the future that enables the set of patient devices 104A through 104*n* and the storage system 106 and the set of doctor devices 108A through 108*n* and the storage system 110 to be coupled to and/or in communication with one another and/or to share resources. In various embodiments, the network 102 can comprise a cloud network (IAN), a SAN (e.g., a storage area network, a small area network, a server area network, and/or a system area network), a wide area network (WAN), a local area network (LAN), a wireless local area network (WLAN), a metropolitan area network (MAN), an enterprise private network (EPN), a virtual private network (VPN), and/or a personal area network (PAN), among other examples of computing networks and/or or sets of computing devices connected together for the purpose of sharing resources that are possible and contemplated herein.

Patient devices 104A through 104*n* (also simply referred individually, in various groups, or collectively as patient device(s) 104) can be any suitable computing hardware and/or software (e.g., a thick client, a thin client, or hybrid thereof) capable of accessing the set of doctor devices 108A through 108*n* and the storage system 110 via the network 102. Each patient device 104, as part of its respective operation, relies on sending I/O requests to the set of doctor devices 108A through 108*n* and the storage system 110 to write data, read data, and/or modify data. Specifically, each patient device 104 can transmit I/O requests to read, write, store, communicate, propagate, and/or transport instructions, data, computer programs, software, code, routines, etc., to the set of doctor devices 108A through 108*n* and the storage system 110 and may comprise at least a portion of a client-server model. In general, the set of doctor devices 108A through 108*n* and the storage system 110 can be accessed by the patient device(s) 104 and/or communication with the set of doctor devices 108A through 108*n* and the storage system 110 can be initiated by the patient device(s) 104 through a network socket (not shown) utilizing one or more inter-process networking techniques.

A patient device 104 may include any suitable computing device that is known or developed in the future that can perform the various functions of a patient device 104 discussed herein. Example patient devices 104 can include, but are not limited to, a cellular telephone, a personal computing device, a computing tablet, a personal digital assistant, a smartwatch, a computing gaming device, and/or a stand-alone computing device, among other types of computing device that are possible and contemplated herein.

Storage system 106 may include any suitable type of storage device and/or system that is known or developed in the future that can store computer-useable data. In various embodiments, a storage system 106 may include one or more non-transitory computer-usable mediums (e.g., readable, writable, etc.), which may include any non-transitory and/or persistent apparatus or device that can contain, store, communicate, propagate, and/or transport instructions, data, computer programs, software, code, routines, etc., for processing by or in connection with a computer processing device.

In various embodiments, the storage system 106 can be considered a patient-device interaction data repository that stores user data and health data, each of which is discussed elsewhere herein. The user data, task data, and/or health data can be encrypted when written to the storage system 106 and decrypted when read from the storage system 106.

Doctor devices 108A through 108n (also simply referred individually, in various groups, or collectively as doctor device(s) 108) can be any suitable computing hardware and/or software (e.g., a thick client, a thin client, or hybrid thereof) capable of accessing the set of patient devices 104 and the storage system 106 via the network 102. Each doctor device 106, as part of its respective operation, relies on sending I/O requests to the set of patient devices 104 and the storage system 106 to write data, read data, and/or modify data. Specifically, each doctor device 108 can transmit I/O requests to read, write, store, communicate, propagate, and/ or transport instructions, data, computer programs, software, code, routines, etc., to the set of patient devices 104 and the storage system 106 and may comprise at least a portion of a client-server model. In general, the set of patient devices 104 and the storage system 106 can be accessed by the doctor device(s) 108 and/or communication with the set of patient devices 104 and the storage system 106 can be initiated by the doctor device(s) 108 through the network socket utilizing the one or more inter-process networking techniques.

A doctor device 108 may include any suitable computing device that is known or developed in the future that can perform the various functions of a doctor device 108 discussed herein. Example doctor devices 108 can include, but are not limited to, a cellular telephone, a personal computing device, a computing tablet, a personal digital assistant, a smartwatch, a computing gaming device, and/or a stand-alone computing device, among other types of computing device that are possible and contemplated herein.

Storage system 110 may include any suitable type of storage device and/or system that is known or developed in the future that can store computer-useable data. In various embodiments, a storage system 110 may include one or more non-transitory computer-usable mediums (e.g., readable, writable, etc.), which may include any non-transitory and/or persistent apparatus or device that can contain, store, communicate, propagate, and/or transport instructions, data, computer programs, software, code, routines, etc., for processing by or in connection with a computer processing device.

In various embodiments, the storage system 110 can be considered a doctor-patient data repository that stores user data and health data, each of which is discussed elsewhere herein. The user data, task data, and/or health data can be encrypted when written to the storage system 110 and decrypted when read from the storage system 110.

Healthcare network 100 can identify and/or track one or more involuntary movement diseases. Example involuntary movement diseases may include, but are not limited to, Tardive Dyskinesia (TD), tremors, Myoclonus, tics (e.g., sudden, repetitive, non-rhythmic motor movements involving discrete muscle groups), Athetosis, and Parkinson's disease, among other involuntary movement diseases that are possible and contemplated herein.

Figure 2:
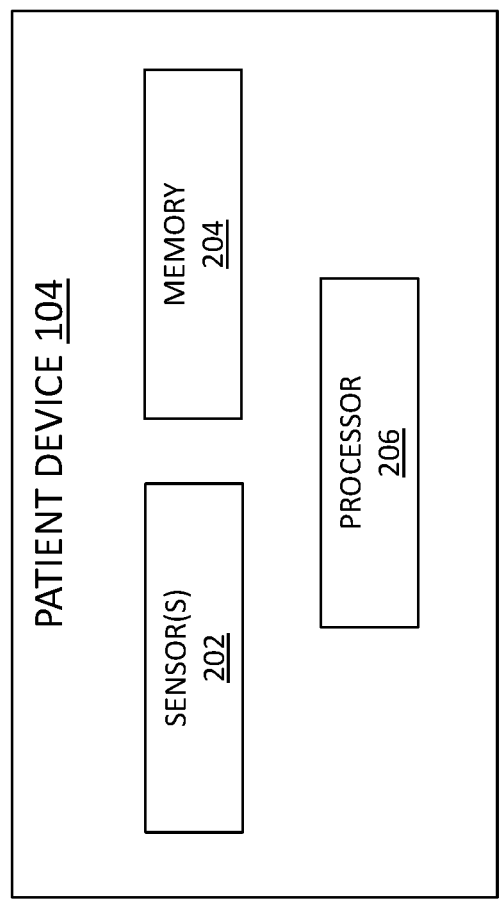
FIG. 2 is a block diagram of one embodiment of a patient device included in the healthcare network of FIG. 1.

Referring to FIG. 2, FIG. 2 is a block diagram of one embodiment of a patient device 104 illustrated in and discussed with reference to FIG. 1. A patient device 104, at least in the illustrated embodiment, includes, among other components, a set of sensors 202, memory 204, and a processor 206.

A sensor 202 may include any suitable hardware and/or software that is capable of detecting the behavior (e.g., movement, motion, handling, and/or pressure, etc.) of a user as the user interacts and/or uses the patient device 104. Further, the hardware and/or software can include or form at least a portion of any suitable type of sensor 202, sensing device, and/or sensing system. Examples of a sensor 202 can include, but are not limited to, a gyroscope, a pressure sensor, a motion sensor, microphone, touchless screen sensor, and/or a camera, among other types of sensor 202 sensing device, and/or sensing system that are possible and contemplated herein.

A set of sensors 202 may include any suitable quantity of sensors 202 that can detect one or more types of behavior of a user as the user interacts and/or uses the patient device 104. In one embodiment, the set of sensors 202 can include a single sensor 202. In various other embodiments, the set of sensors 202 may include two or more sensors 202.

In one embodiment, the set of sensors 202 can include a single type of sensor 202. In other embodiments, the set of sensors 202 can include two or more different types of sensors 202. In additional or alternative embodiments, the set of sensors 202 can include multiple sensors 202 for each different type of sensor 202. For example, a set of sensors 202 can include two or more pressure sensors and two or more gyroscopes, among other combinations of sensors 202 including the same quantity or different quantities of sensor types that are possible and contemplated herein.

In further additional or alternative embodiments, the multiple sensors 202 can be arranged in and/or include a matrix of sensors 202. In some embodiments, the matrix of sensors 202 can detect the behavior of the user with six degrees of freedom as the user interacts with/uses the patient device 104.

The set of sensors 202 are coupled to and/or in communication with memory 204. In various embodiments, the set of sensors 202 is configured to transmit the detected user behavior(s) to memory 204.

Memory 204 may include any suitable hardware and/or software that can at least temporarily store computer-useable data. Further, the hardware and/or software may form and/or include any suitable type of storage device and/or system that is known or developed in the future that can store the computer-useable data. In various embodiments, memory 204 may include one or more non-transitory computer-usable mediums (e.g., readable, writable, etc.), which may include any non-transitory and/or persistent apparatus or device that can contain, store, communicate, propagate, and/or transport instructions, data, computer programs, software, code, routines, etc., for processing by or in connection with a processor 206.

Figure 3B:
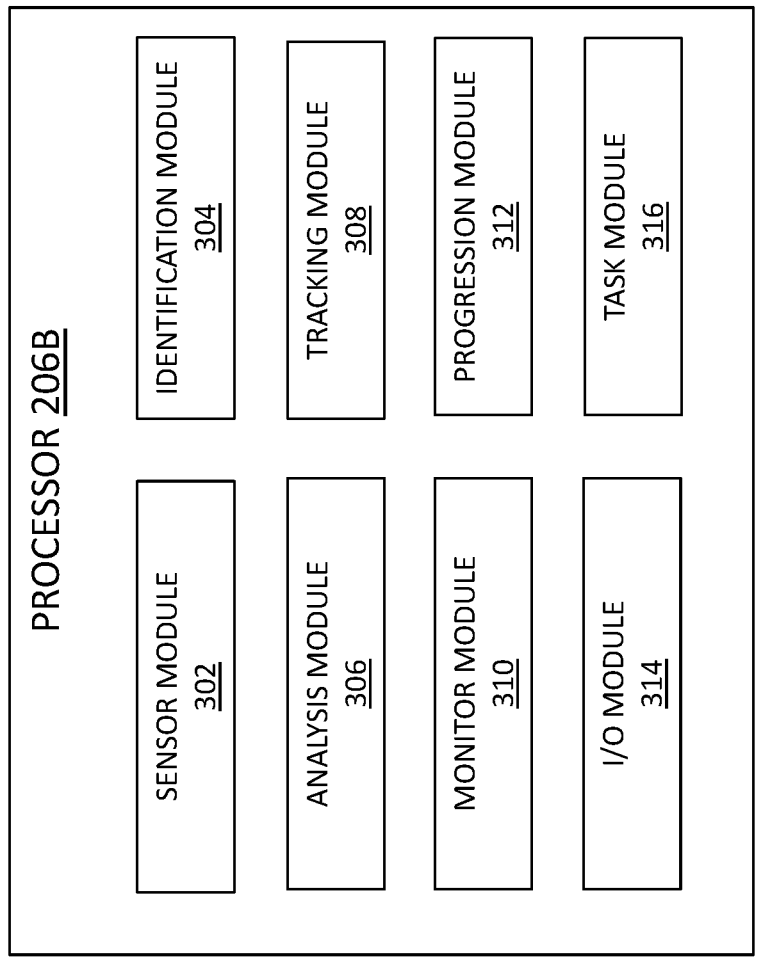

In some embodiments, memory 204 can receive and store data generated by a processor 206 (see e.g., data generated by a sensor module 302, an identification module 304, an analysis module 306, a tracking module 308, a monitor module 310, and/or a progression module 312 in FIG. 3A and/or FIG. 3B), as discussed elsewhere herein. Further, memory 204 can facilitate transmitting the data generated by the processor 206 and stored in memory 204 to a storage system 106. In additional or alternative embodiments, memory 204 can receive and store data (e.g., health data, task data include a set of user tasks, etc.) from the storage system 106, as discussed elsewhere herein. Memory 204 can further receive and store one or more inputs from a user in response to the user performing the set of user tasks as user input data, as further discussed elsewhere herein.

A processor 206 may include any suitable processing hardware and/or software capable of performing computer processes, functions, and/or algorithms. In various embodiments, a processor 206 is configured to facilitate communication between computing components or nodes (e.g., sensor(s) 202, memory 204, storage system 106, doctor device(s) 108, and storage system 110, etc.) in the healthcare system 100.

With reference to FIG. 3A, FIG. 3A is a block diagram of one embodiment of a processor 206A that can be included in a patient device 104 discussed with reference to FIG. 2. At least in the illustrated embodiment, the processor 206A includes, among other components, a sensor module 302 and an identification module 304.

A sensor module 302 may include any suitable hardware and/or software that can manage and/or control the various sensing functions of the set of sensors 202. In one embodiment, the sensor module 302 can operate one or more sensors 202 on a periodic basis. For example, the sensor module 302 can operate the one or more sensors 202 in response to detecting that the user is using one or more particular functions and/or applications of the patient device 104.

In one embodiment, the sensor module 302 can operate one or more sensors 202 on a periodic basis. For example, the sensor module 302 can operate the one or more sensors 202 in response to detecting that the user is using one or more particular functions and/or applications of the patient device 104.

In other embodiments, the sensor module 302 can operate the one or more of the sensors 202 on a continual or substantially continual basis. For example, the sensor module 302 can operate the one or more sensors 202 in response to detecting that the user is using and/or interacting with the patient device 104 (e.g., the user is using any function and/or application of the patient device 104).

In additional or alternative embodiments, the sensor module 302 can operate the one or more sensors 202 in background operations of a processor 206. That is, the sensor(s) 202 and the sensor module 302 can operate and/or function without the user initiating use of the sensor(s) 202 and sensor module 302 and/or knowing that sensor(s) 202 and sensor module 302 are performing their respective operations/functions.

An identification module 304 may include any suitable hardware and/or software that can identify one or more involuntary movements in the user behavior(s) detected by the set of sensors 202. In further embodiments, the identification module 304 can identify voluntary movements in the user behavior(s) detected by the set of sensors 202.

In various embodiments, the identification module 304 can identify an involuntary movement based on one or more characteristics of the user behavior(s) detected by the set of sensors 202. For example, the identification module 304 can match the characteristic(s) of a particular detected user behavior to one or more characteristics of a corresponding involuntary movement of a human, among other identification techniques that are possible and contemplated herein.

Similarly, the identification module 304 can identify a voluntary movement based on one or more characteristics of the user behavior(s) detected by the set of sensors 202. For example, the identification module 304 can match the characteristic(s) of a particular detected user behavior to one or more characteristics of a corresponding voluntary movement of a human, among other identification techniques that are possible and contemplated herein. In this manner, an identification module 304 can differentiate between involuntary movements and voluntary movements of a user interacting with/using the patient device 104.

In additional or alternative embodiments, the identification module 304 performs its various processes in background operations of a processor 206. That is, the identification module 304 can operate and/or function without the user initiating use of the identification module 304 and/or knowing that the identification module 304 is operating.

Referring to FIG. 3B, FIG. 3B is a block diagram of another embodiment of a processor 206B that can be included in a patient device 104 discussed with reference to FIG. 2. A processor 206B can include, among other components, a sensor module 302 and an identification module 304 similar to the various embodiments of a processor 206A discussed elsewhere herein. At least in the illustrated embodiment, the processor 206B further includes, among other components, an analysis module 306, a tracking module 308, a monitor module 310, a progression module 312, an input/output (I/O) module 314, and a task module 316.

An analysis module 306 may include any suitable hardware and/or software that can analyze a set of involuntary movements identified by an identification module 304 to determine whether that a user has an involuntary movement disease and/or exhibits one or more symptoms of an involuntary movement disease. In further embodiments, the analysis module 306 can determine that the set of involuntary movements in the user behavior(s) detected by the set of sensors 202 is/are not characteristic of an involuntary movement disease.

In various embodiments, the analysis module 306 can determine that a user has an involuntary movement disease and/or is exhibiting symptoms of an involuntary disease based on one or more characteristics in the set of involuntary movements identified by an identification module 304. For example, the analysis module 306 can determine that the user has and/or is exhibiting symptoms of an involuntary movement disease by matching one or more characteristic(s) of a set of involuntary movements to the characteristic(s) of a corresponding involuntary movement disease, among other determination techniques that are possible and contemplated herein.

Similarly, the analysis module 306 can determine that a user does not have an involuntary movement disease based on one or more characteristics in the set of involuntary movements identified by an identification module 304. For example, the analysis module 306 can determine that one or more characteristics of a particular identified set of involuntary movements do not match the characteristic(s) of an involuntary movement disease, among other determination techniques that are possible and contemplated herein. In this manner, an analysis module 306 can differentiate between involuntary movements that are characteristic of an involuntary movement disease and involuntary movements that are not symptoms of an involuntary movement disease.

In additional or alternative embodiments, the analysis module 306 performs its various processes in background operations of a processor 206. That is, the analysis module 306 can operate and/or function without the user initiating use of the analysis module 306 and/or knowing that the analysis module 306 is operating.

A tracking module 308 may include any suitable hardware and/or software that can track a set of involuntary movements identified by an identification module 304 over time. That is, the tracking module 308 can differentiate between a set of involuntary movements for a user identified in multiple different periods of time and/or in multiple different periods of usage.

The tracking module 308 can perform its various processes in background operations of a processor 206. That is, the tracking module 308 can operate and/or function without the user initiating use of the tracking module 308 and/or knowing that the analysis module 306 is tracking involuntary movements.

A monitor module 310 may include any suitable hardware and/or software that can monitor a set of involuntary movements tracked by a tracking module 308. In various embodiments, a monitor module 310 can monitor a set of tracked involuntary movements to discern and/or determine differences and/or changes in one or more characteristics of the involuntary movement(s) and/or user behavior(s) defining the one or more characteristics over time. That is, the monitor module 310 can determine differences/changes in one or more characteristics in a set of involuntary movements identified at a particular time and at one or more subsequent times. For example, the monitor module 310 can compare the characteristic(s) of a set of involuntary movements identified at an initial time/usage to one or more characteristics of the set of involuntary movements identified at one or more subsequent times/usages and determine/discern any changes/differences that may be included there between, among other determination techniques that are possible and contemplated herein.

In some embodiments, the comparison can be based on comparing the set of involuntary movements identified at the initial time/usage and the set of involuntary movements identified at the most recent time/usage. In additional or alternative embodiments, the comparison can be based on comparing the set of involuntary movements identified at an intermediate time/usage between the initial time/usage and the set of involuntary movements identified at the most recent time/usage.

The monitor module 310 can perform its various processes in background operations of a processor 206. That is, the monitor module 310 can operate and/or function without the user initiating use of the monitor module 310 and/or knowing that the monitor module 310 is monitoring involuntary movements over time.

A progression module 312 may include any suitable hardware and/or software that can determine the progression or regression of one or more characteristics of a set of involuntary movements and/or one or more involuntary movements in a set of involuntary movements monitored by a monitor module 310. In various embodiments, a progression module 312 can determine progression/regression of the characteristic(s) and/or involuntary movement(s) in a set of monitored in relation to an involuntary movement disease. That is, the progression module 312 can determine whether an involuntary movement disease is staying the same, getting progressively better (e.g., regression), or getting progressively worse based on the differences/changes in one or more characteristics and/or one or more involuntary movements in a monitored set of involuntary movements identified at a particular time and at one or more subsequent times. For example, the progression module 312 can compare the differences/changes determined by the monitor module 310 to characteristic(s) of an involuntary movement disease and determine/discern that there are no changes, the differences/changes are indicative of the involuntary movement disease regressing, or the differences/changes are indicative of the involuntary movement disease progressing, among other determination and/or progression techniques that are possible and contemplated herein.

The progression module 312 can perform its various processes in background operations of a processor 206. That is, the progression module 312 can operate and/or function without the user initiating use of the progression module 312 and/or knowing that the progression module 312 is determining the progression/regression of an involuntary movement disease.

An I/O module 314 may include any suitable hardware and/or software that can receive I/O requests (e.g., read requests, write requests, etc.) and perform I/O operations (e.g., read operations, write operations, etc.) corresponding to the I/O requests. In some embodiments, an I/O module 314 can write data (e.g., user data) generated by the sensor module 302, identification module 304, analysis module 306, tracking module 308, monitor module 310, and/or progression module 312 to memory 204 for at least temporary storage therein.

In additional or alternative embodiments, an I/O module 314 can transmit the user data generated by the sensor module 302, identification module 304, analysis module 306, tracking module 308, monitor module 310, and/or progression module 312 to the storage system 106 for at least temporary storage therein. The data generated by the sensor module 302, identification module 304, analysis module 306, tracking module 308, monitor module 310, and/or progression module 312 can be directly transmitted from the corresponding module to the storage system 106 and/or can be transmitted (e.g., via read/write operations) from memory 204 to the storage system 106.

The data generated by the sensor module 302, identification module 304, analysis module 306, tracking module 308, monitor module 310, and/or progression module 312 can be any suitable data generated by the respective modules that may be relevant to the healthcare of a user. Examples of the data that can be generated by and stored in memory 204 and/or the storage system 106 can include, but is not limited to, sensor data generated by the sensor module 302 that includes the detected user behavior(s), identification data generated by the identification module 304 that includes identified user involuntary movements and/or voluntary movements, analysis data (e.g., diagnosis data) generated by the analysis module 306 that includes an indication of whether the user has one or more characteristics of and/or has an involuntary movement disease, tracking data generated by the tracking module 308 that includes the characteristic(s) and/or one or more involuntary movements of a set of involuntary movements over one or more periods of time and/or periods of usage, monitor data generated by the monitor module 310 that includes discerned and/or determined differences and/or changes in the characteristic(s) of one or more user involuntary movements and/or user behavior(s) defining the one or more characteristics over time, and/or progression data generated by the progression module 312 that includes an indication of whether one or more characteristic of and/or one or more involuntary movements that can define an involuntary movement disease that is or may be attributed to a user is staying the same, regressing, or progressing, among other types of data that may be generated by and received from the sensor module 302, identification module 304, analysis module 306, tracking module 308, monitor module 310, and/or progression module 312 that are possible and contemplated herein.

In some embodiments, an I/O module 314 can receive an I/O request (e.g., a write request) from a storage system 106 to write health data (discussed with reference to processor 404 in FIG. 5) generated by a health care professional (e.g., a doctor, physician's assistant, specialist, etc.) to memory 204. In response to the I/O request, the I/O module 314 can write the health data to memory 204 and/or present the health data to the user via the patient device 104 (e.g., a visual output, and/or an audio output, etc.).

In additional or alternative embodiments, an I/O module 314 can receive an I/O request (e.g., a write request) from the storage system 106 to write task data including a set of user tasks to memory 204. In response to the I/O request, the I/O module 314 can write the task data to memory 204. The I/O module 314 can further present the set of tasks to the user via the patient device 104 (e.g., a visual output, and/or an audio output, etc.) and receive one or more user inputs in response to performing the set tasks, as discussed elsewhere herein. The received user inputs may then be transmitted to memory 204 and/or the storage system 106 for at least temporary storage therein, respectively.

A task module 316 may include any suitable hardware and/or software that can facilitate a user performing a set of tasks assigned to the user by a healthcare professional. In various embodiments, a task module 316 can receive task data including the set of tasks for the user to perform.

In response to receiving the task data, a task module 316 can identify each task included in the set of tasks and facilitate presenting the task(s) to the user. For example, the task module 316 can coordinate with and/or operate in conjunction with an I/O module 314 to present the task(s) to the user via a patient device 104 (e.g., via a visual output and/or an audio output, etc.).

A task may include any suitable exercise that a user can perform on and/or with a patient device 104. In various embodiments, a task may include one or more exercises that cause(s) the user to interact with and/or use a patient device 104 to facilitate detection of one or more involuntary movements and/or voluntary movements (e.g., by a set of sensors 202) exhibited by the user during performance of such one or more exercises. In some embodiments, a task can cause the user to provide user inputs to the patient device 104 related to moving the patient device 104 (e.g., placing the patient device 104 in motion, a finger shaking, etc.), applying pressure and/or a force to one or more portions of the patient device (e.g., touching and/or pressing a screen, etc.), and/or interacting/using the patient device 104 in a manner that can be recorded by a camera, among other types of tasks that can facilitate detection of one or more involuntary movements and/or voluntary movements that are possible and contemplated herein.

The task module 316 can receive one or more inputs from a user in response to the user performing the task(s) on and/or with the patient device 104. The task module 316 can transmit the user input(s) to a set of sensors 202 and/or the set of sensors 202 can independently detect the one or more tasks, from which a sensor module 302 can generate sensor data, as discussed elsewhere herein.

With reference to FIG. 4, Figure is a block diagram of one embodiment of a doctor device 108 illustrated in and discussed with reference to FIG. 1. A doctor device 108, at least in the illustrated embodiment, includes, among other components, memory 402, and a processor 404.

Memory 402 may include any suitable hardware and/or software that can at least temporarily store computer-useable data. Further, the hardware and/or software may form and/or include any suitable type of storage device and/or system that is known or developed in the future that can store the computer-useable data. In various embodiments, memory 402 may include one or more non-transitory computer-usable mediums (e.g., readable, writable, etc.), which may include any non-transitory and/or persistent apparatus or device that can contain, store, communicate, propagate, and/or transport instructions, data, computer programs, software, code, routines, etc., for processing by or in connection with a processor 404.

In some embodiments, memory 402 can receive and store data generated by a processor 404 (see e.g., health data and/or task data generated by a medical professional, etc.). Further, memory 402 can facilitate transmitting the data generated by the processor 404 and stored in memory 402 to a storage system 110. In additional or alternative embodiments, memory 402 can receive and store data generated by a patient device 104 (e.g., sensor data, identification data, analysis data, tracking data, monitor data, progression data, and/or user input data, etc.) from the storage system 110.

A processor 404 may include any suitable processing hardware and/or software capable of performing computer processes, functions, and/or algorithms. In various embodiments, a processor 404 is configured to facilitate communication between computing components or nodes (e.g., memory 402, storage system 110, patient device(s) 104, and storage system 106, etc.) in the healthcare system 100.

Figure 5:
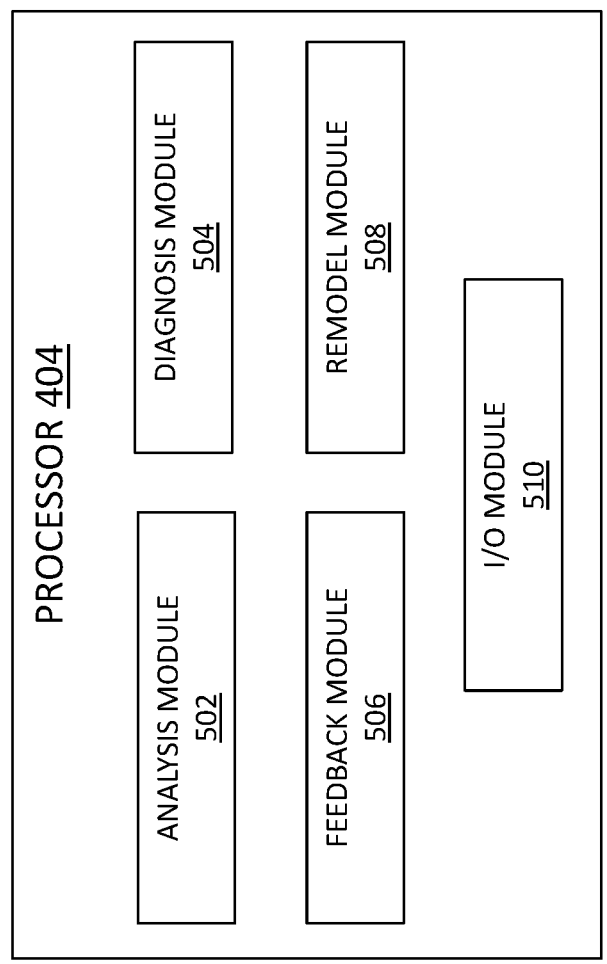
FIG. 5 is a block diagram of one embodiment of a processor included in the doctor device of FIG. 4.

Referring to FIG. 5, FIG. 5 is a block diagram of one embodiment of a processor 404 that can be included in a doctor device 108 discussed with reference to FIG. 4. At least in the illustrated embodiment, a processor 404 can include, among other components, an analysis module 502, a diagnosis module 504, a feedback module 506, and a remodel module 508, and an I/O module 510.

An analysis module 502 may include any suitable hardware and/or software that can analyze data generated by a patient device 104. In various embodiments, an analysis module 502 can analyze sensor data, identification data, analysis data, tracking data, monitor data, progression data, and/or user input data, etc. generated by the patient device 104 to determine whether and/or verify that the detected user behavior is involuntary/voluntary movements based on one or more characteristics of the detected user behavior.

A diagnosis module 504 may include any suitable hardware and/or software that can determine whether and/or verify that a user has an involuntary movement disease and/or exhibits one or more symptoms of an involuntary movement disease. In various embodiments, a diagnosis module 504 can make the determination based on a set of involuntary movements identified by an analysis module 502.

In various embodiments, the diagnosis module 504 can determine that a user has an involuntary movement disease and/or is exhibiting symptoms of an involuntary disease based on one or more characteristics in the set of involuntary movements identified by the analysis module 502. For example, the diagnosis module 504 can determine that the user has and/or is exhibiting symptoms of an involuntary movement disease by matching one or more characteristic(s) of a set of involuntary movements to the characteristic(s) of a corresponding involuntary movement disease, among other determination techniques that are possible and contemplated herein.

Similarly, the diagnosis module 504 can determine that a user does not have an involuntary movement disease based on one or more characteristics in the set of involuntary movements identified by an analysis module 502. For example, the diagnosis module 504 can determine that one or more characteristics of set of involuntary movements do not match the characteristic(s) of an involuntary movement disease, among other determination techniques that are possible and contemplated herein. In this manner, a diagnosis module 504 can differentiate between involuntary movements that are characteristic of an involuntary movement disease and involuntary movements that are not symptoms of an involuntary movement disease.

The diagnosis module 504 can generate diagnosis data, which can include any suitable data related to diagnosing a patient. In some embodiments, diagnosis data can include, but is not limited to, data indicating that a patient has or does not have one or more involuntary movement diseases, data indicating that a patient has or does not have one or more symptoms/characteristics of an involuntary movement disease, and/or data indicating that a patient has or does not have one or more symptoms of an involuntary movement disease that is/are progressing, regressing, or staying the same, among other types of data related to diagnosing an involuntary movement disease that are possible and contemplated herein.

A feedback module 506 may include any suitable hardware and/or software that can generate health data. The health data can include data generated by a diagnosis module 504 (e.g., diagnosis data) and/or data input from a healthcare professional (e.g., supplemental diagnosis data, medication data, prescription data, instruction data, recommendation data, treatment data, etc.), among other types of data that are relevant to a doctor-patient relationship that are possible and contemplated herein.

A remodel module 508 may include any suitable hardware and/or software that can generate and/or receive task data from a medical professional. A remodel module 508, in some embodiments, can generate and/or select one or more tasks of a set of user tasks for inclusion in the task data. In additional or alternative embodiments, a remodel module 508 can receive the set of tasks for inclusion in the task data from a medical professional.

A task for inclusion in the set of tasks can be based on one or more symptoms/characteristics of an involuntary movement disease that a user is suspected of having. For example, a task may be selected and/or generated based on one or more exercises that would cause a user (e.g., a patient) to exhibit one or more involuntary movements that are characteristic of the suspected involuntary movement disease.

An I/O module 510 may include any suitable hardware and/or software that can receive I/O requests (e.g., read requests, write requests, etc.) and perform I/O operations (e.g., read operations, write operations, etc.) corresponding to the I/O requests. In some embodiments, an I/O module 510 can write data generated by the analysis module 502, diagnosis module 504, feedback module 506, and/or remodel module 508 to memory 402 for at least temporary storage therein.

In additional or alternative embodiments, an I/O module 510 can transmit the data generated by the analysis module 502, diagnosis module 504, feedback module 506, and/or remodel module 508 to the storage system 110 for at least temporary storage therein. The data generated by the analysis module 502, diagnosis module 504, feedback module 506, and/or remodel module 508 can be directly transmitted from the corresponding module to the storage system 110 and/or can be transmitted (e.g., via read/write operations) from memory 402 to the storage system 110.

The data generated by the analysis module 502, diagnosis module 504, feedback module 506, and/or remodel module 508 can be any suitable data generated by the respective modules that may be relevant to the healthcare of a user. Examples of the data that can be generated by and stored in memory 204 and/or the storage system 106 can include, but is not limited to, analysis data generated by the analysis module 502 that includes the identified user involuntary movements and/or voluntary movements, diagnosis data generated by the diagnosis module 504, feedback data generated by the feedback module 506, and/or task data generated and/or receive by the remodel module 508, among other types of data that may be generated by and received from the analysis module 502, diagnosis module 504, feedback module 506, and/or remodel module 508 that are possible and contemplated herein.

In some embodiments, an I/O module 510 can receive an I/O request (e.g., a write request) from a storage system 110 to write user data generated by a patient device 104 to memory 402. In response to the I/O request, the I/O module 510 can write the user data to memory 402 and/or present the user data to a healthcare professional via the doctor device 108 (e.g., a visual output, and/or an audio output, etc.).

In additional or alternative embodiments, an I/O module 510 can receive an I/O request (e.g., a write request) from the storage system 110 to read task data including a set of user tasks from memory 402. In response to the I/O request, the I/O module 510 can write the task data to the storage system 110.

Figure 6:
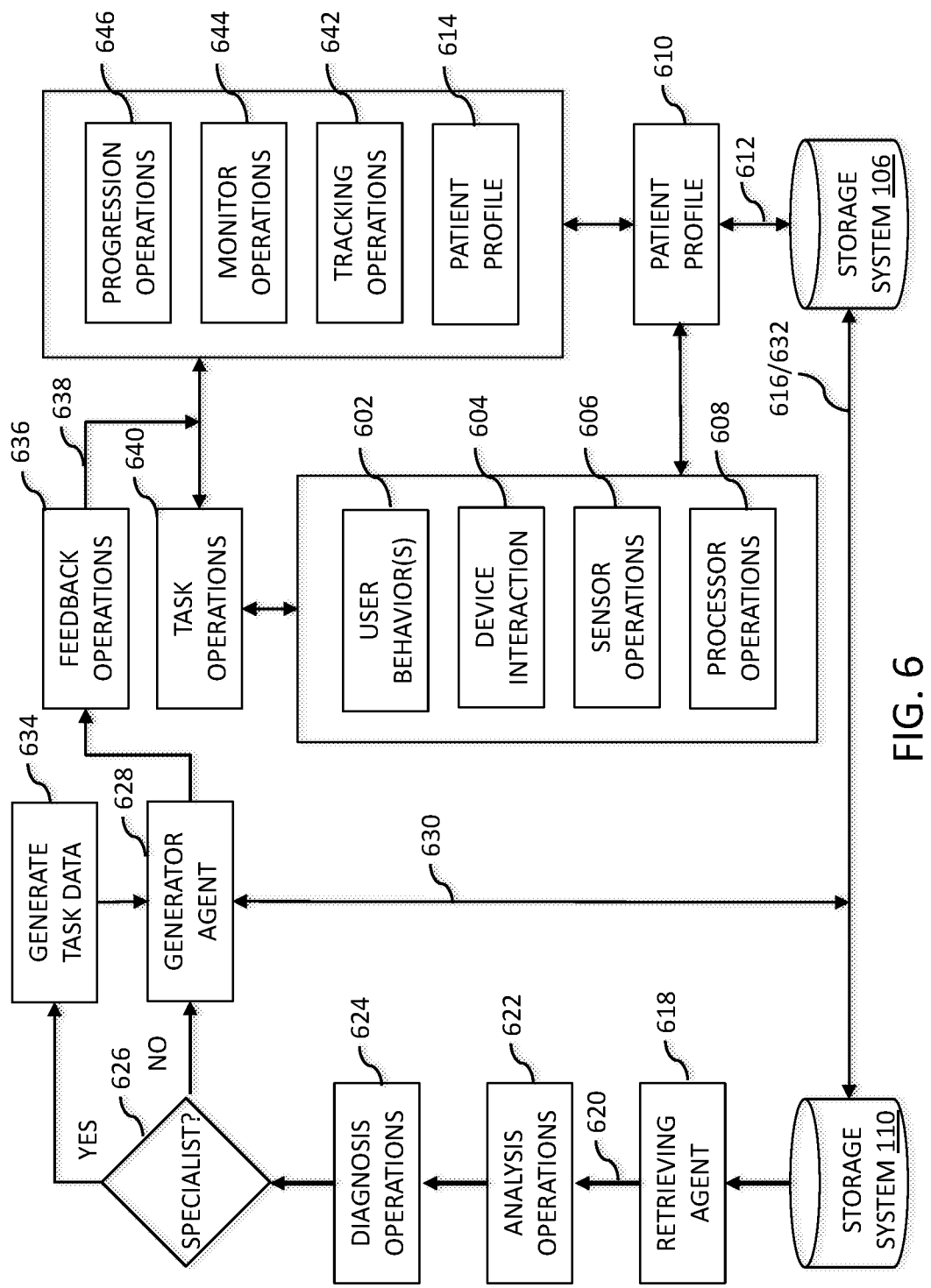
FIG. 6 is a flow diagram illustrating the operations of one embodiment of the healthcare network of FIG. 1.

With reference to FIG. 6, FIG. 6 is a flow diagram illustrating the operations 400 of one embodiment of a health network 100. At least in the illustrated embodiment, the operations 400 can begin by patient device 602 determining/detecting one or more behaviors of a patient/user (block 602) as the user interacts with and/or uses the patient device 104 (block 604).

A set of sensors 202 can detect the behavior(s) of the user as the user interacts and/or uses the patient device 104 via sensor operations (block 606). A processor 206 can perform processor operations to generate user data (e.g., sensor data, identification data, analysis data, tracking data, monitor data, progression data, and/or user input data, etc.) in response to the detected user behavior(s) (block 608).

The processor device 206 can utilize storage device selection agent operations (block 610) to transfer the user data to a storage system 106 (transfer operations 612). The processor device 206 can further utilize storage device selection agent operations (block 610) to locate patient profile data associated with the user corresponding to the user data and associate the patient profile data with the user data (block 614).

The storage system 106 can transfer the user data to a storage system 110 (transfer operations 616). A storage device retrieving agent can perform retrieving operations to retrieve the user data from the storage system 110 (block 618) and transmit the user data to an analysis module 504 (transfer operations 620).

The analysis module 504 can perform analysis operations that analyze sensor data, identification data, analysis data, tracking data, monitor data, progression data, and/or user input data, etc. in the user data to determine whether and/or verify that the detected user behavior is involuntary/voluntary movements based on one or more characteristics of the detected user behavior included in the user data and generate doctor analysis data based thereon (block 622). A diagnosis module 506 can perform diagnosis operations to generate diagnosis data and/or receive diagnosis data from a medical professional that can include data indicating that a patient has or does not have one or more involuntary movement diseases, data indicating that a patient has or does not have one or more symptoms/characteristics of an involuntary movement disease, and/or data indicating that a patient has or does not have one or more symptoms of an involuntary movement disease that is/are progressing, regressing, or staying the same based on the doctor analysis data (block 624).

The diagnosis operations can query whether the opinion of a medical specialist (e.g., a neurologist) should be sought (block 626). An answer to the query can be based on, for example, the complexity of the diagnosis, the characteristic(s) of the user behavior(s), and/or the characteristic(s) of the involuntary movement disease that the user may have. In some embodiments, the answer is based on the confidence in the accuracy of the diagnosis data.

In response to determining that the opinion of a medical specialist should not be sought (e.g., a "NO" to the query in block 626), a storage device generator agent, which can be included as at least a portion of a feedback module 506, can generate health data (block 628), which can include the diagnosis data and, optionally, other types of health data. The storage device generator agent can transfer the health data to the storage system 110 (transfer operations 630) and the storage system 110 can further transfer the health data to the storage system 106 (transfer operations 632).

In response to determining that the opinion of a medical specialist should be sought (e.g., a "YES" to the query in block 626), a specialist and/or a remodel module 508 can generate task data that includes one or more tasks for the user to perform to obtain supplemental user behavior(s) (block 634). The task data can be included in the health data generated by the storage device generator agent (block 628).

The feedback module 506 can combine the task data with other health data from a medical professional (block 636) and transmit at least the task data to the user device 104 (transfer operations 638). A task module 316 in the user device 104 can present the set of tasks in the task data to the user (block 640) and the user can once again interact with the patient device 104 (block 602) and the operations 400 may then repeat for one or more iterations based on inputs by the user in responding to the set of tasks.

A tracking module 308 can track the user behavior(s) over time (block 642) and a monitor module 310 can monitor the tracked user behaviors to determine/discern any changes/differences in the user behavior(s) and/or involuntary movement(s) that may have occurred between one or more periods of time and/or periods of use (block 644). A progression module 312 can determine whether an involuntary movement disease and/or one or more symptoms of an involuntary movement disease have stayed the same, progressed, or regressed (block 646). The tracking data, monitor data, and/or progression data generated by the tracking module 308, monitor module 310, and/or progression module 312, respectively, can be transmitted to the user device 104 (transfer path 648) and/or transmitted to the storage system 106 and be included as at least a portion of the user data via storage device selection agent (block 610 and transfer path 612).

Figure 7:
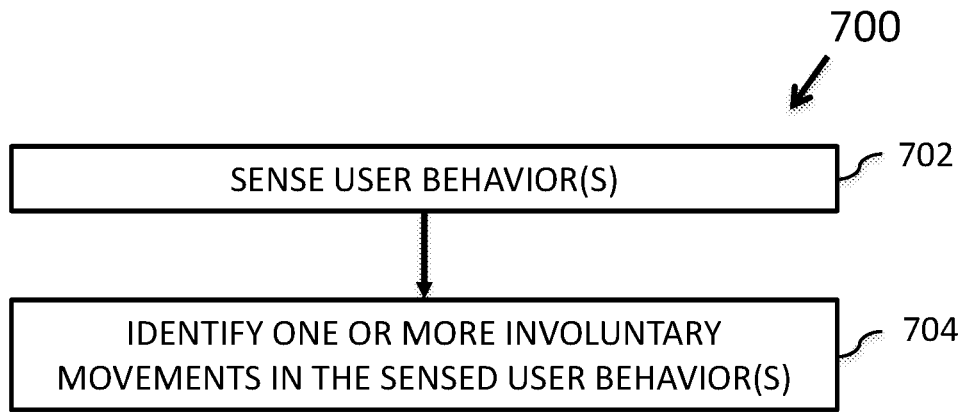
FIG. 7 is a schematic flow chart diagram illustrating one embodiment of a method for identifying involuntary movement diseases.

Referring to FIG. 7, FIG. 7 is a schematic flow chart diagram illustrating one embodiment of a method 700 for identifying involuntary movement diseases. At least in the illustrated embodiment, method 700 can begin by a set of sensors 202 sensing one or more behaviors of a user (block 702). The sensed behavior(s) can include any of the user behaviors discussed elsewhere herein.

A processor 206, via an identification module 304, can identify one or more involuntary movements for the user based on the sensed behavior(s) (block 704). The involuntary movement(s) can be identified using any of the techniques and/or processes discussed elsewhere herein. In various embodiments, the sensing operations and/or the identification operations can be performed in background operations of the sensor(s) 202 and/or processor 206.

Figure 8:
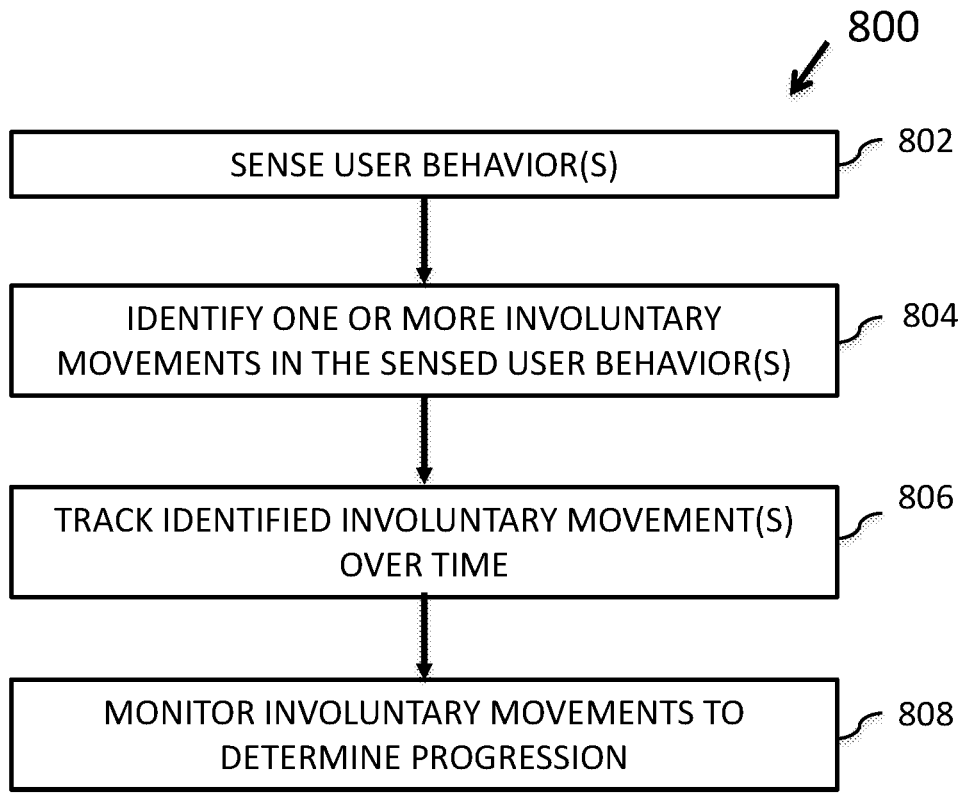
FIG. 8 is a schematic flow chart diagram illustrating one embodiment of a method for identifying and tracking involuntary movement diseases.

With reference to FIG. 8, FIG. 8 is a schematic flow chart diagram illustrating one embodiment of a method 800 for identifying and tracking involuntary movement diseases. At least in the illustrated embodiment, method 800 can begin by a set of sensors 202 sensing one or more behaviors of a user (block 802). The sensed behavior(s) can include any of the user behaviors discussed elsewhere herein.

A processor 206, via an identification module 304, can identify one or more involuntary movements for the user based on the sensed behavior(s) (block 804). The involuntary movement(s) can be identified using any of the techniques and/or processes discussed elsewhere herein.

Using a tracking module 308, the processor 206 can track the identified involuntary movement(s) over time (block 806). The identified involuntary movement(s) can be tracked over any suitable amount of time, periods of time, and/or periods of use, as discussed elsewhere herein.

The processor 206, via a monitor module 310, can monitor the tracked involuntary movement(s) to determine one or more differences/changes over time, which can form the basis for determining whether an involuntary movement disease is staying the same, progressing, or regressing (block 808). The monitor module 310 can determine the one or more differences/changes over time by performing monitor operations, as discussed elsewhere herein.

The involuntary movement disease staying the same, progressing, or regressing can be determined by a progression module 312 of the processor 206 performing progression operations, as discussed elsewhere herein. In various embodiments, the sensing operations, the identification operations, the tracking operations, monitor operations, and/or progression operations can be performed in background operations of the sensor(s) 202 and/or processor 206.

Figure 9:
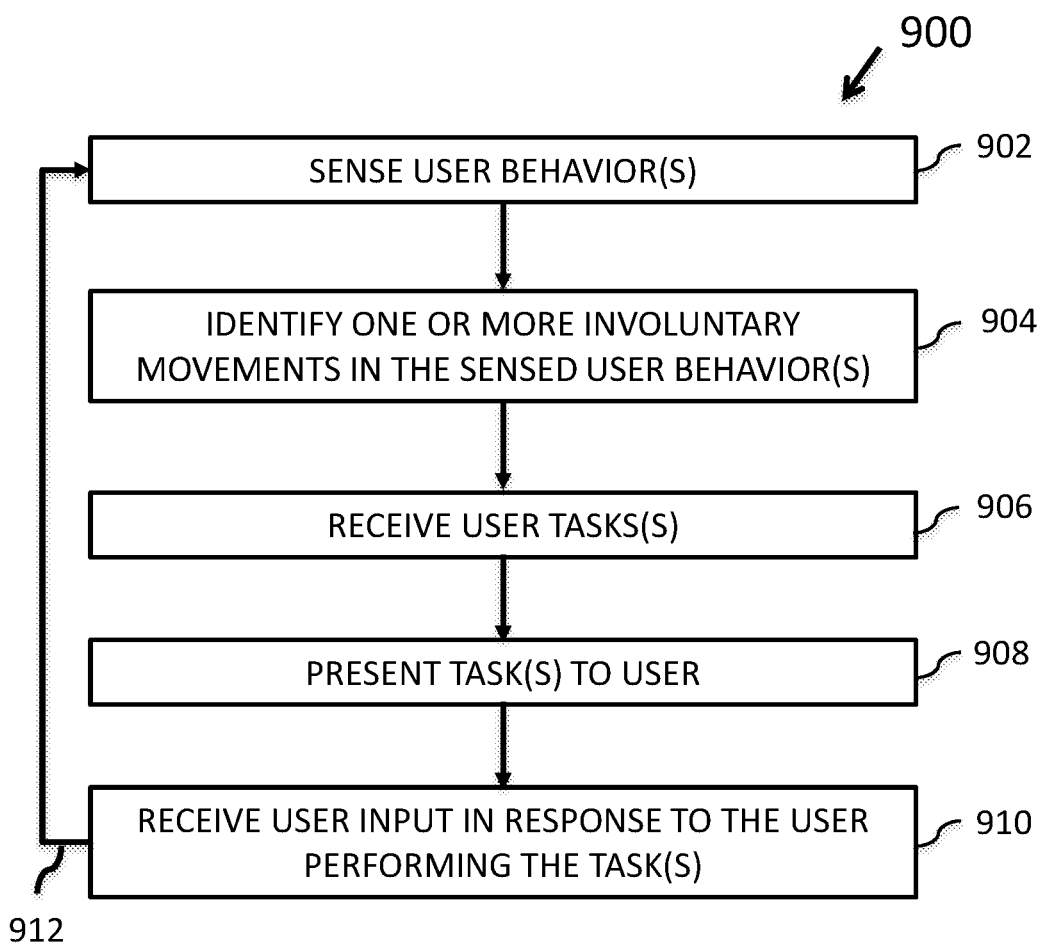
FIG. 9 is a schematic flow chart diagram illustrating another embodiment of a method for identifying and tracking involuntary movement diseases.

Referring to FIG. 9, FIG. 9 is a schematic flow chart diagram illustrating another embodiment of a method 900 for identifying and tracking involuntary movement diseases. At least in the illustrated embodiment, method 900 can begin by a set of sensors 202 sensing one or more behaviors of a user (block 902). The sensed behavior(s) can include any of the user behaviors discussed elsewhere herein.

A processor 206, via an identification module 304, can identify one or more involuntary movements for the user based on the sensed behavior(s) (block 904). The involuntary movement(s) can be identified using any of the techniques and/or processes discussed elsewhere herein.

Further, the processor 206 can a set of tasks for the user to perform (block 906). The set of tasks can be included in task data received from a doctor device 108, as discussed elsewhere herein.

Using a task module 316, the processor 206 can present the one or more tasks to the user (block 908). The task(s) can be visually and/or audibly presented to the user, as discussed elsewhere herein.

The processor 206, can receive one or more user inputs as the user performs the presented task(s) (block 910). The user inputs can be any of the user inputs discussed elsewhere herein. The sensor(s) 202 can then sense one or more behaviors of the user via the user inputs similar to the operations in block 902 (return 912). In various embodiments, the sensing operations and/or the identification operations can be performed in background operations of the sensor(s) 202 and/or processor 206.

The described embodiments are to be considered in all respects only as illustrative and not restrictive. The scope of the technology is, therefore, indicated by the appended claims rather than by the foregoing description. All changes which come within the meaning and range of equivalency of the claims are to be embraced within their scope.

What is claimed is:

1. An apparatus, comprising:
   a task module that:
      presents a first set of tasks to a user for the user to perform on the apparatus, and
      receives a first set of user inputs in response to the user performing the first set of tasks;
   a set of sensors that sense behavior of the user while the user performs tasks on the apparatus; and
   an identification module that identifies involuntary movement patterns for the user based on one or more characteristics of the sensed behavior while the user performs the tasks on the apparatus;
   an input/output (I/O) module that, in response to being unable to determine whether the user has one of a plurality of involuntary movement diseases based on a first set of involuntary movement patterns corresponding to one or more characteristics of a first sensed behavior exhibited by the user while performing the first set of tasks:
      transmits the first set of involuntary movement patterns corresponding to the one or more characteristics of the first sensed behavior to a remote device of a medical specialist, and
      receives, in response to the transmittal, a second set of tasks for the user to perform on the apparatus from the medical specialist;
   a remodel module that:
      presents the second set of tasks to the user for the user to perform on the apparatus, and
      receives a second set of user inputs from the user in response to the user performing the second set of tasks on the apparatus, the second set of user inputs including one or more characteristics defining a second sensed behavior exhibited by the user while performing the second set of tasks; and
   an analysis module that:
      determines that the user has one of the plurality of involuntary movement diseases based on the one or more of characteristics defining the second sensed behavior matching one or more of corresponding characteristics of a particular one of the plurality of involuntary movement diseases, or
      determines that the user does not have one of the plurality of involuntary movement diseases based on the one or more of characteristics defining the second sensed behavior not matching corresponding characteristics of any of the plurality of involuntary movement diseases, and
      in response to the determining that the user has one of the plurality of involuntary movement diseases, diagnoses the user as having the particular one of the plurality of involuntary movement diseases,
   wherein at least a portion of each of said modules comprises one or more of a set of hardware circuits, a set of programmable hardware devices, and executable code stored on a set of non-transitory computer-readable storage media.

2. The apparatus of claim 1, wherein the set of sensors includes a matrix of sensors comprising two or more different ones of a gyroscope, a pressure sensor, a motion sensor, and a camera.

3. The apparatus of claim 1, wherein the set of sensors and the identification module are configured to function when the apparatus is in use by the user.

4. The apparatus of claim 1, wherein the analysis module is further configured to:
   analyze the identified involuntary movement patterns to facilitate determining whether the user has the one of the plurality of involuntary movement diseases, and
   attribute the one of the plurality of involuntary movement diseases to the user based on the determination.

5. The apparatus of claim 4, further comprising:
   a tracking module that tracks the involuntary movement patterns over time; and
   a progression module that analyzes the tracked involuntary movement patterns to determine a state of the one of the plurality of involuntary movement diseases attributed to the user.

6. The apparatus of claim 5, wherein the state comprises a progression of the particular one of the plurality of involuntary movement diseases.

7. The apparatus of claim 5, wherein the state comprises a regression of the particular one of the plurality of involuntary movement diseases.

8. The apparatus of claim 5, wherein the state comprises a progression or a regression of the particular one of the plurality of involuntary movement diseases.

9. The apparatus of claim 1, wherein the set of sensors and the identification module operate as background functions of the apparatus.

10. A method, comprising:
   presenting a first set of tasks to a user for the user to perform on the apparatus;
   receiving a first set of user inputs in response to the user performing the first set of tasks;
   sensing, by a set of sensors of a computing device, behavior of the user while the user performs the first set of tasks;
   identifying, by a processor of the computing device, involuntary movement patterns for the user based on one or more characteristics of the sensed behavior while the user performs the first set of tasks;
   in response to being unable to determine whether the user has one of a plurality of involuntary movement diseases based on a first set of involuntary movement patterns corresponding to one or more characteristics of a first sensed behavior exhibited by the user while performing the first set of tasks:
      transmitting the first set of involuntary movement patterns corresponding to the one or more characteristics of the first sensed behavior to a remote device of a medical specialist, and
      receiving, in response to the transmittal, a second set of tasks for the user to perform on the apparatus from the medical specialist;
   presenting the second set of tasks to the user for the user to perform on the apparatus;

receiving a second set of user inputs from the user in response to the user performing the second set of tasks on the apparatus, the second set of user inputs including one or more characteristics defining a second sensed behavior exhibited by the user while performing the second set of tasks;

determining one of:
- the user has one of the plurality of involuntary movement diseases based on the one or more of characteristics defining the second sensed behavior matching one or more of corresponding characteristics of a particular one of the plurality of involuntary movement diseases, and
- the user does not have one of the plurality of involuntary movement diseases based on the one or more of characteristics defining the second sensed behavior not matching corresponding characteristics of any of the plurality of involuntary movement diseases; and in response to the determining that the user has one of the plurality of involuntary movement diseases, diagnosing the user as having the particular one of the plurality of involuntary movement diseases.

11. The method of claim 10, wherein the behavior is sensed and identified in background operations of the computing device.

12. The method of claim 10, further comprising:
tracking the involuntary movement patterns over time.

13. The method of claim 12, further comprising:
monitoring the tracked involuntary movement patterns to determine if the particular one of the plurality of involuntary movement diseases has progressed.

14. The method of claim 12, further comprising:
monitoring the tracked involuntary movement patterns to determine if the particular one of the plurality of involuntary movement diseases has regressed.

15. A computer program product comprising a computer-readable storage medium including program instructions embodied therewith, the program instructions executable by a processor to cause the processor to:

present a first set of tasks to a user for the user to perform on an apparatus;

receive a first set of user inputs in response to the user performing the first set of tasks;

sense, by a set of sensors, behavior of the user while the user performs the first set of tasks;

identify involuntary movement patterns for the user based on one or more characteristics of the sensed behavior while the user performs the first set of tasks;

in response to being unable to determine whether the user has one of a plurality of involuntary movement diseases based on a first set of involuntary movement patterns corresponding to one or more characteristics of a first sensed behavior exhibited by the user while performing the first set of tasks:
- transmit the first set of involuntary movement patterns corresponding to the one or more characteristics of the first sensed behavior to a remote device of a medical specialist, and
- receive, in response to the transmittal, a second set of tasks for the user to perform on the apparatus from the medical specialist;

present the second set of tasks to the user for the user to perform on the apparatus;

receive a second set of user inputs from the user in response to the user performing the second set of tasks on the apparatus, the second set of user inputs including one or more characteristics defining a second sensed behavior exhibited by the user while performing the second set of tasks;

determine one of:
the user has one of the plurality of involuntary movement diseases based on the one or more of characteristics defining the second sensed behavior matching one or more of corresponding characteristics of a particular one of the plurality of involuntary movement diseases, and the user does not have one of the plurality of involuntary movement diseases based on the one or more of characteristics defining the second sensed behavior not matching corresponding characteristics of any of the plurality of involuntary movement diseases; and in response to the determining that the user has one of the plurality of involuntary movement diseases, diagnosing the user as having the particular one of the plurality of involuntary movement diseases.

16. The computer program product of claim 15, wherein the behavior is sensed and identified in background operations of the computing device.

17. The computer program product of claim 15, wherein the processor is further configured to:
track the involuntary movement patterns over time.

18. The computer program product of claim 17, wherein the processor is further configured to:
monitor the tracked involuntary movement patterns to determine if the particular one of the plurality of involuntary movement diseases has progressed.

19. The computer program product of claim 17, wherein the processor is further configured to:
monitor the tracked involuntary movement patterns to determine if the particular one of the plurality of involuntary movement diseases has regressed.

* * * * *